(12) United States Patent
Araki et al.

(10) Patent No.: US 11,083,482 B2
(45) Date of Patent: Aug. 10, 2021

(54) ULTRASONIC PROBE

(71) Applicant: OLYMPUS CORPORATION, Hachioji (JP)

(72) Inventors: Hiroyuki Araki, Hachioji (JP); Kiichiro Sawada, Hachioji (JP); Takamitsu Sakamoto, Hachioji (JP); Ken Fujisaki, Sagamihara (JP); Hideto Yoshimine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 195 days.

(21) Appl. No.: 16/395,476

(22) Filed: Apr. 26, 2019

(65) Prior Publication Data
US 2019/0247070 A1 Aug. 15, 2019

Related U.S. Application Data

(63) Continuation of application No. PCT/JP2016/082190, filed on Oct. 28, 2016.

(51) Int. Cl.
*A61B 17/32* (2006.01)
*A61B 17/16* (2006.01)
*A61B 17/00* (2006.01)

(52) U.S. Cl.
CPC .. *A61B 17/320068* (2013.01); *A61B 17/1631* (2013.01); *A61B 17/1659* (2013.01);
(Continued)

(58) Field of Classification Search
CPC ........ A61B 17/1675; A61B 17/320068; A61B 2017/320073
See application file for complete search history.

(56) References Cited

U.S. PATENT DOCUMENTS 5,443,475 A * 8/1995 Auerbach .......... A61B 17/1608
600/564
8,287,485 B2 10/2012 Kimura et al.
(Continued)

FOREIGN PATENT DOCUMENTS

JP S57-074020 U 5/1982
JP 2005-152098 A 6/2005
(Continued)

OTHER PUBLICATIONS

Jan. 31, 2017 Search Report issued in International Patent Application No. PCT/JP2016/082190.

*Primary Examiner* — Nicholas W Woodall
(74) *Attorney, Agent, or Firm* — Oliff PLC

(57) ABSTRACT

A method of performing a procedure on a meniscus, via an ultrasonic surgical tool. The ultrasonic tool includes a probe capable of transmitting ultrasonic vibration from a proximal end toward a front end. The probe includes a bent portion that is inclined with respect to a longitudinal axis of the probe, and a procedure portion that is disposed at the front end of the probe and has a plurality of cutting surfaces. The method includes: inserting the probe in a body; moving the probe through a space in between the femur and the tibia to position the procedure portion adjacent to the horizontal rupture in the meniscus; positioning a cutting surface of the procedure portion on a posterior portion of the meniscus; and resecting the horizontal rupture along an inclination of the meniscus to form an inclined resection plane.

10 Claims, 11 Drawing Sheets

(52) U.S. Cl.
CPC .......... *A61B 17/1675* (2013.01); *A61B 17/32* (2013.01); *A61B 17/32002* (2013.01); *A61B 2017/00402* (2013.01); *A61B 2017/320008* (2013.01); *A61B 2017/320072* (2013.01); *A61B 2017/320073* (2017.08); *A61B 2017/320077* (2017.08)

(56) References Cited

U.S. PATENT DOCUMENTS

| | | | |
|---|---|---|---|
| 9,730,709 | B2 | 8/2017 | Yoshimine |
| 9,730,710 | B2 | 8/2017 | Yoshimine |
| 9,839,437 | B2 | 12/2017 | Yoshimine |
| 2017/0100137 | A1* | 4/2017 | Ueda ................. A61B 17/1675 |
| 2017/0273708 | A1* | 9/2017 | Sakamoto ...... A61B 17/320068 |
| 2017/0281152 | A1* | 10/2017 | Kennedy, III ..... A61B 17/0401 |

FOREIGN PATENT DOCUMENTS

| | | | |
|---|---|---|---|
| WO | 2010/087060 A1 | 8/2010 | |
| WO | 2016/111054 A1 | 7/2016 | |

\* cited by examiner

ULTRASONIC PROBE

This application is a continuation of International Application No. PCT/JP2016/082190, filed on Oct. 28, 2016, the entire contents of which are incorporated herein by reference.

BACKGROUND

The present disclosure relates to an ultrasonic probe that is used to perform a procedure on a target site for procedure in a joint based on ultrasonic vibrations.

Typically, an arthroscopic surgery is known in which portals are opened at about two positions near a joint; a rigid endoscope representing an arthroscope and a therapeutic apparatus are inserted from the portals; the inside of the joint is filled with a circulating water meant to be used in a joint surgery; and a procedure is performed while checking the video displayed on a monitor.

As far as the therapeutic apparatus is concerned, an ultrasonic device is proposed that has an ultrasonic vibrator installed therein, that performs ultrasonic output using an ultrasonic probe, and that performs arbitrary procedures based on ultrasonic vibrations.

In such an ultrasonic probe, a procedure unit is installed at the front end of the probe main body that extends in a linear manner. Usually, when an operator holds the ultrasonic probe, a cutting surface made of a corrugated surface is formed on the underside of the procedure unit.

Examples of an arthroscopic surgery include a surgical procedure performed on the ruptured meniscus of a knee joint. The ultrasonic probe that undergoes ultrasonic vibrations performs the procedure of cutting the ruptured portion and fixing the shape. The meniscus is sandwiched in between the femur and the tibia of the knee joint; and, depending on the site therein, is called an anterior portion, a middle portion, a posterior horn, and a posterior portion, for example. Consider an example of performing a procedure on the targets for procedure such as the posterior portion or the posterior horn and the anterior portion or the anterior horn. In the case of inserting the ultrasonic probe from the same portal, if the positions of the damaged portions are different in the anteroposterior direction, then a situation may occur in which the cutting surface of the procedure portion either cannot make contact with the target site for procedure or does not make contact at an appropriate angle.

In such a case, the ultrasonic probe needs to be replaced with another one or, if replacement is not possible, the position of opening the portal needs to be adjusted; or a new portal needs to be opened.

SUMMARY

According to one aspect of the present disclosure, there is provided a method for performing a procedure on a meniscus, via an ultrasonic surgical tool. The ultrasonic surgical tool may include a probe formed in an elongated shaft shape and capable of transmitting ultrasonic vibration from a proximal end to a front end. The probe may include a bent portion that is inclined with respect to a longitudinal axis of a probe main body, and a procedure portion that is disposed at the front end of the probe and that has a plurality of cutting surfaces.

The method may include inserting the probe in a body; moving the probe through a space between a femur and a tibia to position the procedure portion adjacent to a horizontal rupture in the meniscus; positioning a cutting surface of the procedure portion of the probe on posterior portion of the meniscus; and resecting the horizontal rupture along an inclination of the meniscus to form an inclined resection plane.

The above and other features, advantages and technical and industrial significance of this disclosure will be better understood by reading the following detailed description of presently preferred embodiments of the disclosure, when considered in connection with the accompanying drawings.

DETAILED DESCRIPTION

Exemplary embodiments of an ultrasonic probe of an ultrasonic surgical tool are described below with reference to the accompanying drawings.

Figure 1:
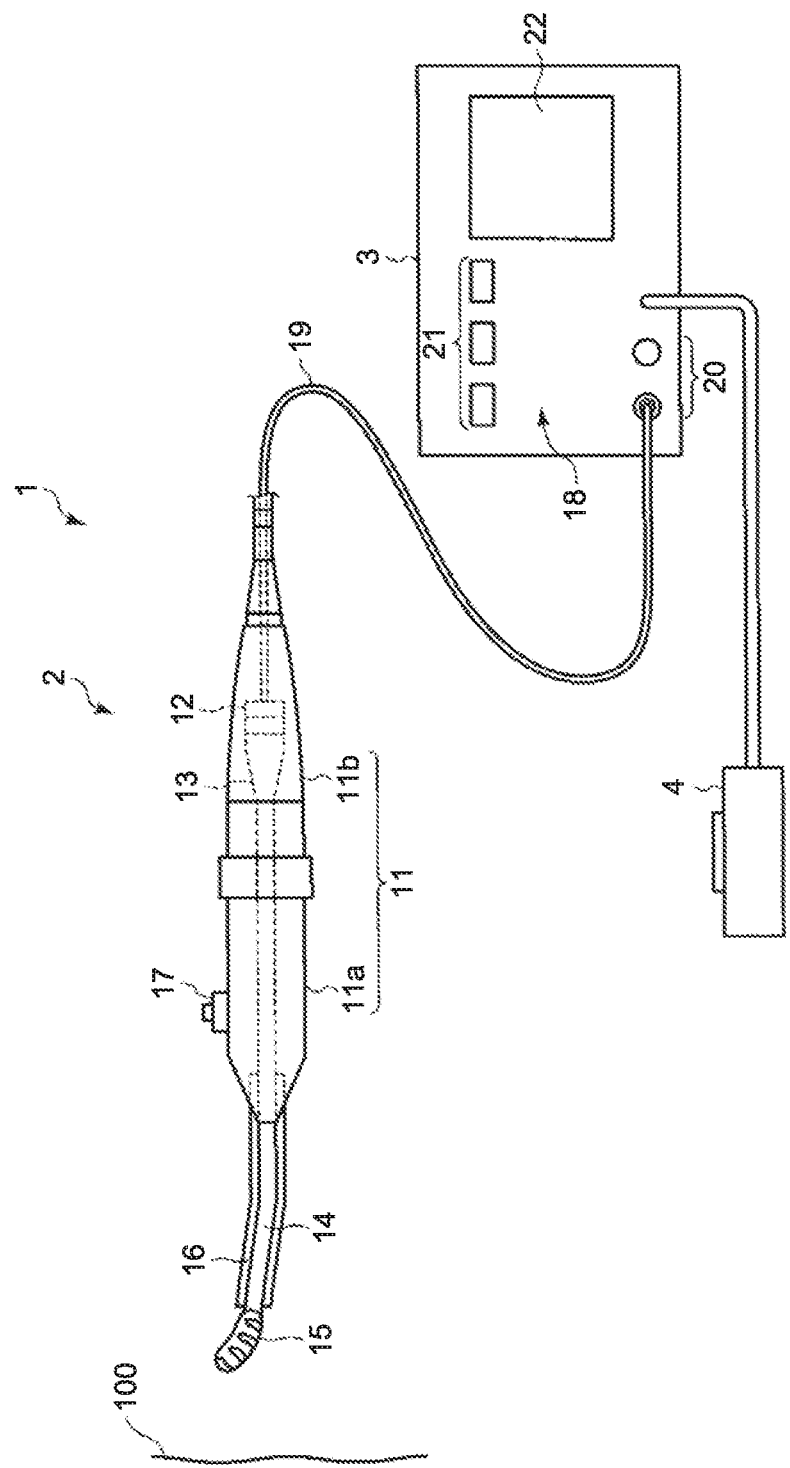
FIG. 1 is a diagram illustrating an exemplary system configuration of an ultrasonic surgical tool system according to an embodiment.

FIG. 1 is a diagram illustrating an exemplary system configuration of the ultrasonic surgical tool system according to an embodiment.

An ultrasonic surgical tool system 1 according to the present embodiment mainly includes an ultrasonic surgical tool 2; an electrical power source 3; and a foot switch 4 that is used to instruct turning on or turning off the ultrasonic vibrations. The ultrasonic surgical tool 2 and the electrical power source 3 are connected by a cable 19 that enables supply of driving power and communication of control signals. In the electrical power source 3, a plurality of connectors 20 is disposed on an anterior surface 18 for enabling establishment of connection with the cable 19, various operation switches 21, and a display screen 22 that is used to display the information necessary for procedures. Moreover, depending on the procedure or the details of the surgery, the electrical power source 3 is separately used in combination with an endoscopic system.

The ultrasonic surgical tool 2 includes a device main body 11 and an ultrasonic probe 14. The device main body 11 has a tubular shape with a holdable diameter, and includes a housing 11a through which the ultrasonic probe 14 is disposed and an ultrasonic vibrator unit (an ultrasonic wave generating unit) 11b that is detachably attached to the housing 11a. Inside the ultrasonic vibrator unit 11b, an ultrasonic wave generating unit 12 that is made of ultrasonic vibrators such as piezoelectric bodies is housed along with a horn 13 that is meant for efficiently transmitting the ultrasonic waves. When the ultrasonic vibrator unit 11b is attached to the housing 11a, the proximal end of the ultrasonic probe 14 and the front end of the horn 13 are sonically connected, and the ultrasonic vibrations generated in the ultrasonic wave generating unit 12 are transmitted to a procedure portion 15 (described later) of the ultrasonic probe 14. On the top surface of the housing 11a is disposed an operation switch 17 that is used instruct turning on or turning off the ultrasonic vibrations according to finger operations. Thus, the foot switch 4 has an equivalent function to the operation switch 17.

The ultrasonic probe 14 is an elongated rod-like shaft member (probe main body) that transmits the ultrasonic vibrations, and is made of a metallic material such as a titanium alloy. Moreover, to the proximal end of the ultrasonic probe 14, the front end of the horn 13 is sonically connected; and, to the front end of the ultrasonic probe 14, the procedure portion 15 is disposed in an integrated manner. Furthermore, the ultrasonic probe 14 has a curvature (a curved portion) that becomes bowed or bends in such a way that, when an operator holds the ultrasonic probe 14 in the normal holding pattern in which the cutting surface is on the underside, the ultrasonic probe 14 bends upward at a position more on the proximal end of the probe main body than the procedure portion 15. Because of the bending, the procedure portion 15 becomes more raised obliquely upward than usual.

The ultrasonic probe 14 is covered by a sheath 16 for an arbitrary length starting from the housing 11a. The sheath 16 is not closely attached to the ultrasonic probe 14 but is disposed with a small clearance gap from the ultrasonic probe 14 so as to prevent attenuation of the ultrasonic vibrations. Moreover, the sheath 16 is fixed to the front end side of the housing 11a at the nodal position of the ultrasonic vibrations. As a result of disposing the sheath 16, in case there is contact with sites other than the target for procedure or contact with other surgical tools or an endoscope, the effect of the contact can be eliminated and the devices and the sites can be protected.

Given below is the explanation of a surgery system that includes an ultrasonic surgical tool and an endoscopic system.

Figure 2:
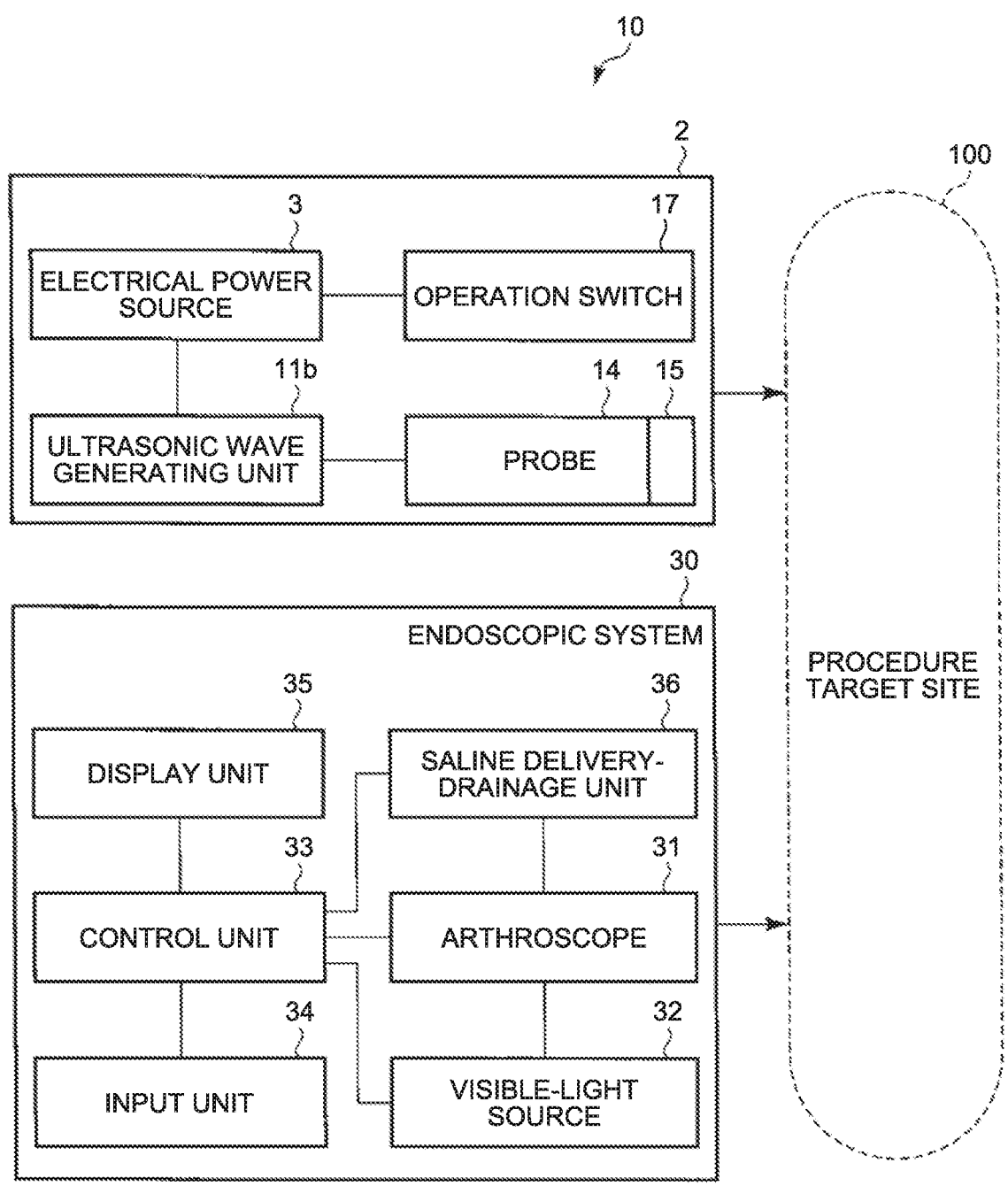
FIG. 2 is a diagram illustrating an exemplary configuration of a surgery system that includes an ultrasonic surgical tool according to an embodiment.

FIG. 2 is a diagram illustrating an exemplary configuration of the surgery system that includes an ultrasonic surgical tool according to an exemplary embodiment. A surgery system 10 according to an exemplary embodiment is configured with the ultrasonic surgical tool 2 and an endoscopic system 30 that includes an arthroscope.

As described earlier, the ultrasonic surgical tool 2 includes the ultrasonic wave generating unit 12, the ultrasonic probe 14, the electrical power source 3, and the operation switch 17.

The endoscopic system 30 is configured with the following: an arthroscope 31 that is made of a rigid endoscope representing a type of endoscope; a visible-light source 32 that functions as the light source of illumination light and that emits visible illumination light; a control unit 33 that controls the entire endoscopic system 30; an input unit 34 such as a keyboard or a touch-sensitive panel; a display unit 35 that displays surgery information containing the photographed surgery status; and a saline delivery-drainage unit 36 that delivers, drains, and perfuses a normal saline solution in the surroundings of a procedure target site 100. In the present embodiment, the saline delivery-drainage unit 36 is configured to perform delivery and drainage of a normal saline solution at the location for procedure via the arthroscope 31. However, alternatively, the configuration can be such that a perfusing medium including a normal saline solution is delivered and drained from the ultrasonic surgical tool 2.

Figure 3:
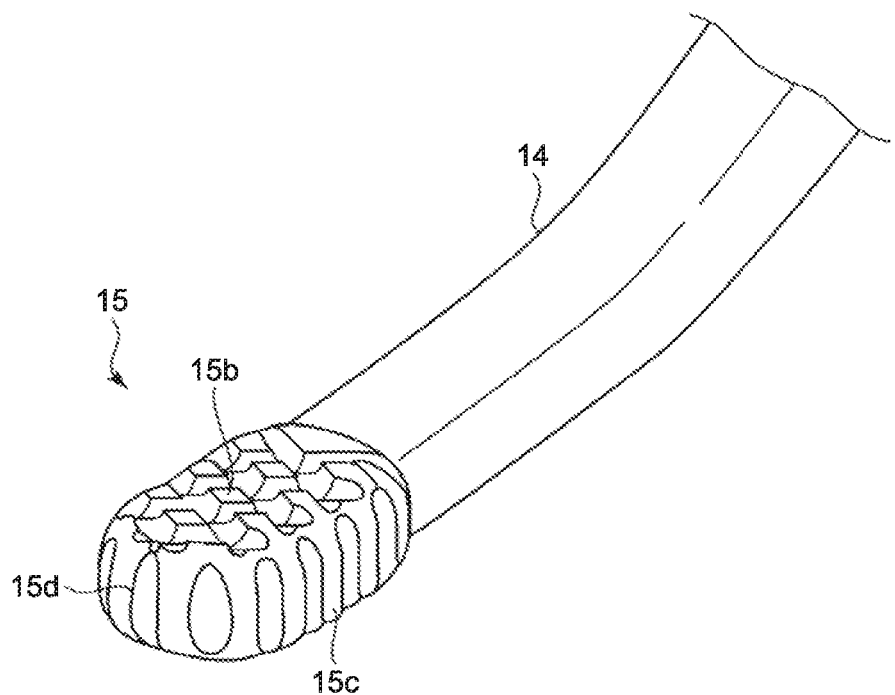
FIG. 3 is a diagram illustrating the external shape of a procedure portion of an ultrasonic probe according to the embodiment, when viewed from an obliquely upward direction.
Figure 4:
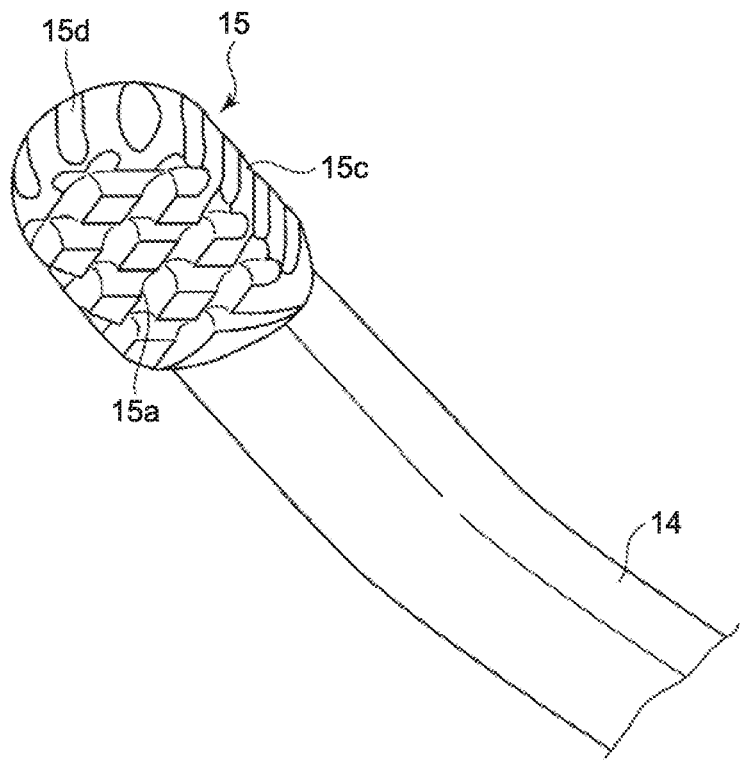
FIG. 4 is a diagram illustrating the external shape of the procedure portion illustrated in FIG. 3, when viewed from an obliquely downward direction.

Explained below with reference to FIGS. 3 and 4 is a structure of the procedure portion 15 of the ultrasonic probe 14. FIG. 3 is a diagram illustrating the external shape of the procedure portion of the ultrasonic probe according to an exemplary embodiment, when viewed from an obliquely upward direction. FIG. 4 is a diagram illustrating the external shape of the procedure portion illustrated in FIG. 3, when viewed from an obliquely downward direction.

The procedure portion 15 according to the present embodiment is cuboid in shape; has a bone cutting function and a cartilage cutting function based on ultrasonic vibrations as described later; and is capable of performing the desired surgical procedure (mainly the resection procedure) on the procedure target site (or the procedure target location) 100. Meanwhile, as long as the procedure portion is substantially cuboid in shape, it serves the purpose. Moreover, the procedure portion has a flat shape.

Of the procedure portion 15, the top surface and the under surface (the principal surfaces) are rectangular in shape with rounded corners. Moreover, the thickness of the procedure portion 15 is such that it can pass through the space in between narrow joints (in the case of a knee joint, the space in between the femur and the tibia) and can reach the target site for procedure. There is no restriction on the thickness, and it can be appropriately set depending on the intended usage. Regarding the probe main body of the ultrasonic probe 14 too, the length thereof is set according to the position of the target site for procedure.

As illustrated in FIGS. 3 and 4, in the procedure portion 15, a cutting surface 15$a$ [a first main cutting surface] that is made of a corrugated surface having a crosshatch pattern due to a plurality of U-shaped grooves is formed on the lower principal surface. In an identical manner, a cutting surface 15$b$ [a second main cutting surface] that is made of a corrugated surface having the same crosshatch pattern is formed on the upper principal surface. The arrangement of U-shaped grooves is such that a parallel flounder pattern, a crosshatch pattern, or a twill line pattern is formed. Moreover, the U-shaped grooves either can be arranged at regular intervals or can be arranged with different intervals set therebetween.

Moreover, on both lateral surfaces of the procedure portion 15, lateral cutting surfaces 15$c$ are formed in which a plurality of U-shaped grooves is arranged in a seriate flounder pattern in the vertical direction (the thickness direction). Moreover, on the anterior surface (the apical surface) too, an apical cutting surface 15$d$ is formed in which a plurality of U-shaped grooves is arranged in a flounder pattern.

Meanwhile, as far as the cutting surfaces of the procedure portion 15 according to the present embodiment are concerned, the cutting surfaces can be formed on the above-mentioned five surfaces excluding the surface connected to the probe main body. From among the cutting surfaces; three cutting surfaces, namely, the first main cutting surface 15$a$ formed on the underside and the lateral cutting surfaces 15$c$ formed on both lateral surfaces represent reference surfaces for cutting that are fundamentally essential in cutting procedures, and hence are called "reference cutting surfaces". On the other hand, in the procedure portion 15, the second main cutting surface formed on the top surface and the apical cutting surface formed on the apical surface are formed only if necessary and are required depending on the procedure details, and hence are called "selective cutting surfaces". This line of thinking is based on the following presumption: regarding an ultrasonic probe having excess cutting surfaces formed thereon that are not used according to the procedure details, the operator needs to ensure that the unused cutting surfaces of such an ultrasonic probe does not come in contact with and cause damage to the surrounding sites. In that regard, in order to be able to deal with the procedure details, the second main cutting surface and the apical cutting surface can be selectively formed depending on the procedure details. For that reason, those cutting surfaces are called selective cutting surfaces.

Moreover, when an operator holds the ultrasonic probe 14 in the normal holding pattern in which the cutting surface 15$a$ (described later) is on the underside, the front end side of the ultrasonic probe 14 is bent upward in such a way that the probe main body bends backward at a position away by about 10 mm from the front end of the procedure portion 15. Meanwhile, the corrugated pattern formed on each cutting surface of the ultrasonic probe 14 is not limited to the arrangement described above, and can be appropriately modified according to the intention of the procedure.

The procedure portion 15 of the ultrasonic probe 14 performs mechanical cutting according to minor sliding to which ultrasonic vibrations are applied. Herein, the amount of scraping can be adjusted according to the strength of the press against the procedure target site 100 (i.e., depending on the pressing pressure). That is, the scraping amount is controlled according to the adjustments made by the operator, thereby enabling efficient cutting and resection. In the following explanation, in the case of performing cutting or performing a procedure using the procedure portion 15, it is assumed that the procedure portion 15 undergoes ultrasonic vibrations even if it is not explicitly mentioned. Moreover, although the ultrasonic surgical tool 2 according to the present embodiment is configured without a mechanism for delivering and draining a perfusing medium, it is alternatively possible to dispose a mechanism for delivering and draining a perfusing medium depending on the intended usage.

Figure 5:
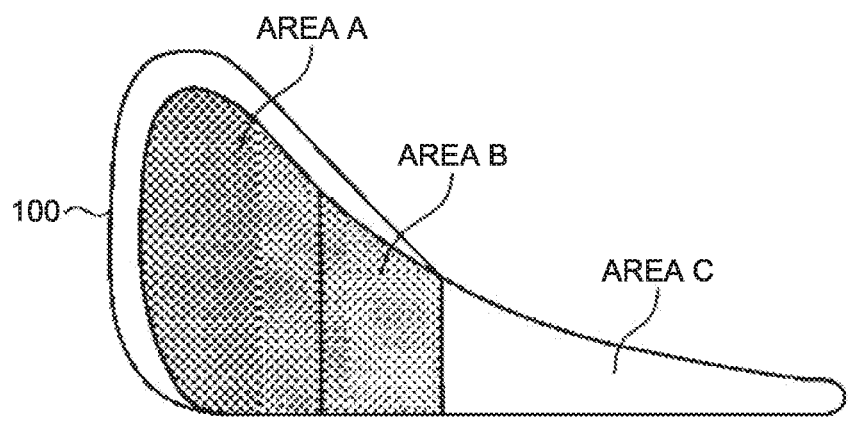
FIG. 5 is a diagram illustrating a cross-section structure of the meniscus.
Figure 6:
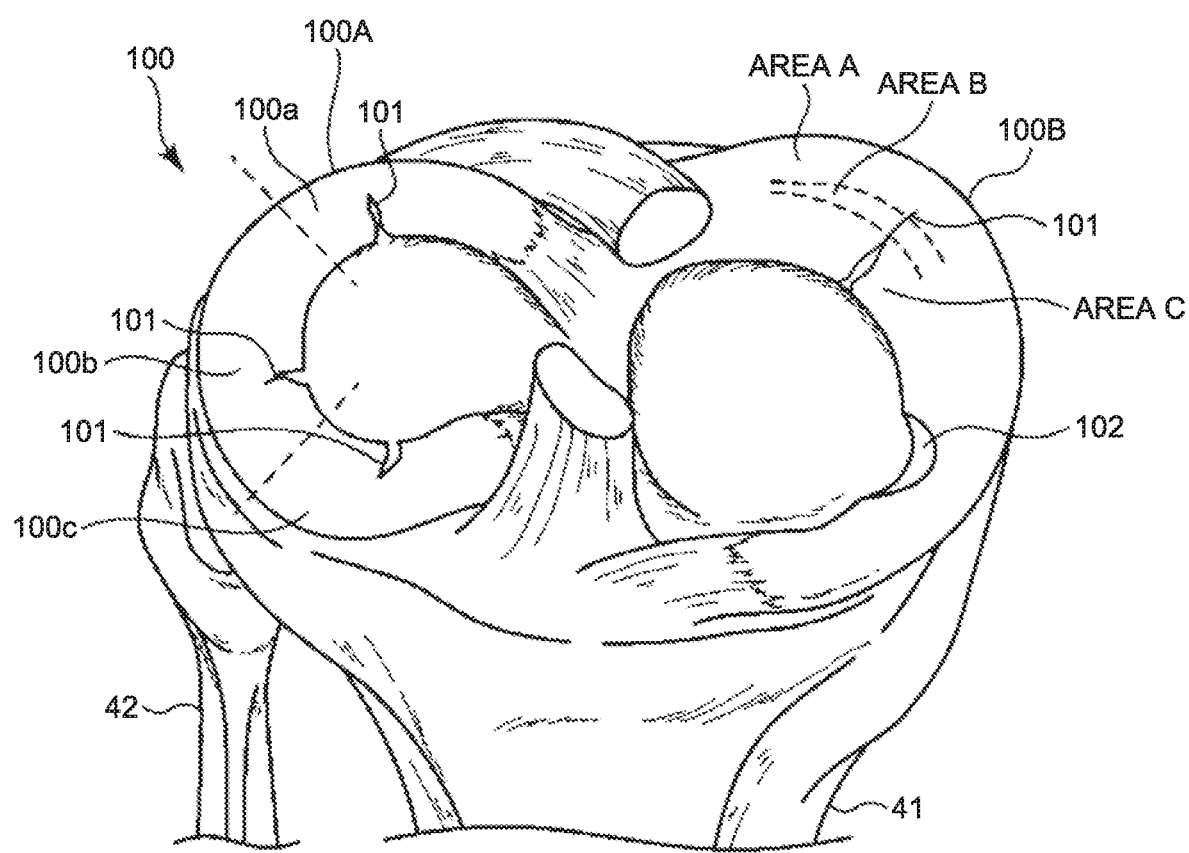
FIG. 6 is a diagram illustrating an overall structure of the meniscus on which a procedure is to be performed using the ultrasonic probe.

Given below is the explanation of an example of a procedure performed on a meniscus that represents an example of the target for procedure of the ultrasonic surgical tool 2 according to the present embodiment. FIG. 5 is a diagram illustrating a cross-section structure of the meniscus. FIG. 6 is a diagram illustrating an overall structure of the meniscus.

As illustrated in FIG. 5, in the cross-section of the meniscus 100, a dense-blood-flow area A [blood circulation field: dense-blood-flow area (red zone)] is present on the outer periphery in which there is a large amount of blood flow (a large number of blood vessels), and an area B [blood circulation field: a coarse-blood-flow area (white-red zone)] is present toward the inside of the arc in which there is a smaller in amount of blood flow than in the area A. Moreover, on the inside of the area B, an area C [no-blood-circulation field: a no-blood-flow area (white zone)] is present in which there is no blood flow at all. In case the meniscus 100 is damaged, the areas A and B in which there is blood flow can be regenerated. Hence, the damaged surfaces are fixed using the ultrasonic probe 14, and a suture procedure is performed. However, in case the area C representing a no-blood-flow area without any blood flow is damaged, it cannot be regenerated. Hence, a resection procedure is performed using the ultrasonic probe 14.

For example, as illustrated in FIG. 6, if a horizontal rupture 101 reaching the blood flow area A is developed near the posterior portion of a medial meniscus 100B; the rupture of the no-blood-flow area C is resected to form an inclined resection plane, a procedure is performed on the ruptured surfaces of the dense-blood-flow area A and the coarse-blood-flow area B using the ultrasonic probe 14, and suturing is performed once the blood dries.

On the other hand, in case a horizontal rupture is developed only within the range of the no-blood-flow area C, the ruptured location is resected to form an inclined resection plane 102. In order to form the inclined resection plane, it becomes necessary to adjust the manner of abutment (i.e., the angle of surface contact) of the ultrasonic probe 14 (described later).

Meanwhile, the inclination of the resection plane, which is formed using the ultrasonic probe 14, is used to avoid concentration of and enable dispersion of the stress attributed to a femur 43. More particularly, in a normal meniscus, the top surface making contact with the femur as illustrated in FIG. 5 is an inclined surface, thereby enabling dispersion of the stress being applied from the femur 43. However, if resection is performed using a conventional tool such as a punch, it results in the formation of a cross-sectional surface that is vertically cut from the top surface of the meniscus, thereby leading to the formation of a horn portion. Since the internal condyle of the femur and the external condyle of the femur are round in shape, it becomes easier for the stress to get concentrated at the horn portion of the meniscus, which may lead to new damage. In order to prevent such concentration of the stress, it is important to perform resection in such a way that the resection plane 102 is an inclined surface having an inclination opposing the internal condyle and the external condyle.

Moreover, as illustrated in FIG. 6, the meniscus 100 includes a lateral meniscus 100A and the medial meniscus 100B against which the medial condyle and the lateral condyle of the femur abut. The lateral meniscus 100A is divided, starting from the dorsal side, into a posterior portion 100a, a body portion (middle portion) 100b, and an anterior portion 100c. The medial meniscus 100B is divided, starting from the dorsal side, into parts named as a posterior horn, a posterior portion, a middle portion, an anterior portion, and an anterior horn. When portals are formed on the anterior side of the body, in order for the ultrasonic probe 14 to perform a procedure by reaching the posterior portion of the lateral meniscus 100A and to reach the posterior portion and the posterior horn of the medial meniscus 100B, the ultrasonic probe 14 needs to pass through the space in between the femur and the tibia. Meanwhile, regarding an arthroscopic surgery (described later), the explanation is given about an example in which the horizontal ruptures 101 are developed in the target sites for procedure such as the posterior portion 100a, the middle portion 100b, and the anterior portion 100c of the lateral meniscus 100A as illustrated in FIG. 6.

Figure 7:
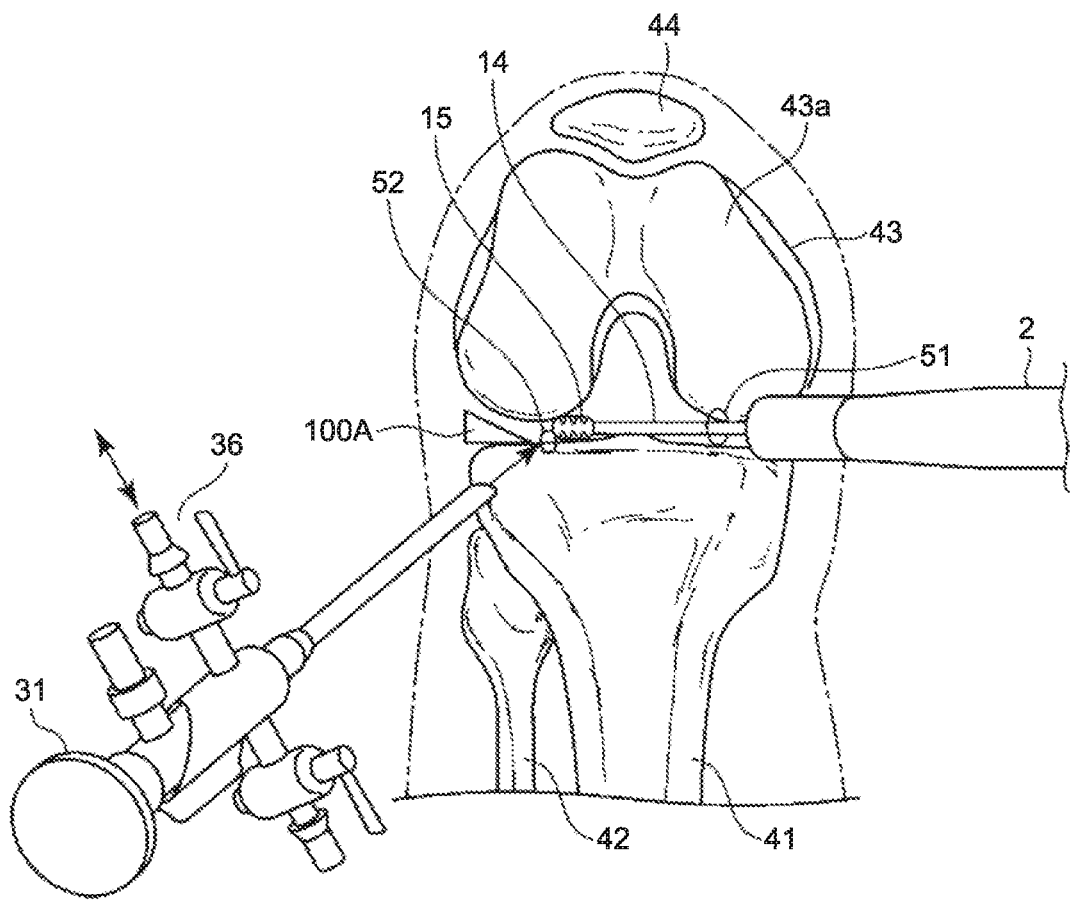
FIG. 7 is a diagram that conceptually illustrates an arthroscopic surgery performed using an ultrasonic surgical tool.
Figure 8:
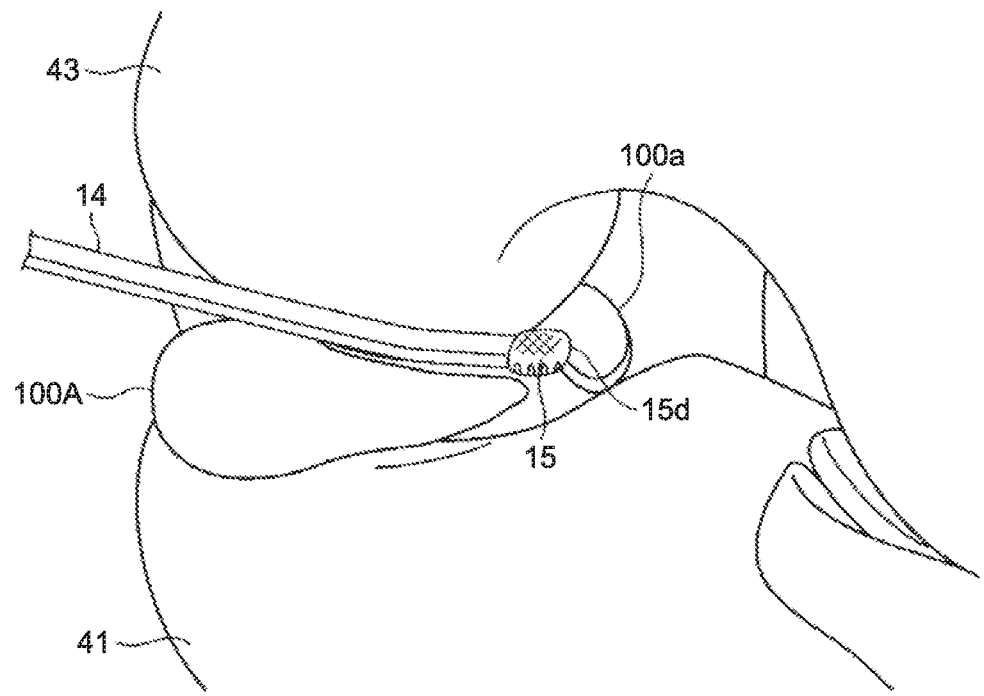
FIG. 8 is a diagram illustrating a situation in which a target site for procedure present in the posterior portion of the lateral meniscus between joints is subjected to a procedure using the front end side of the cutting portion formed on the underside of a procedure portion.
Figure 9:
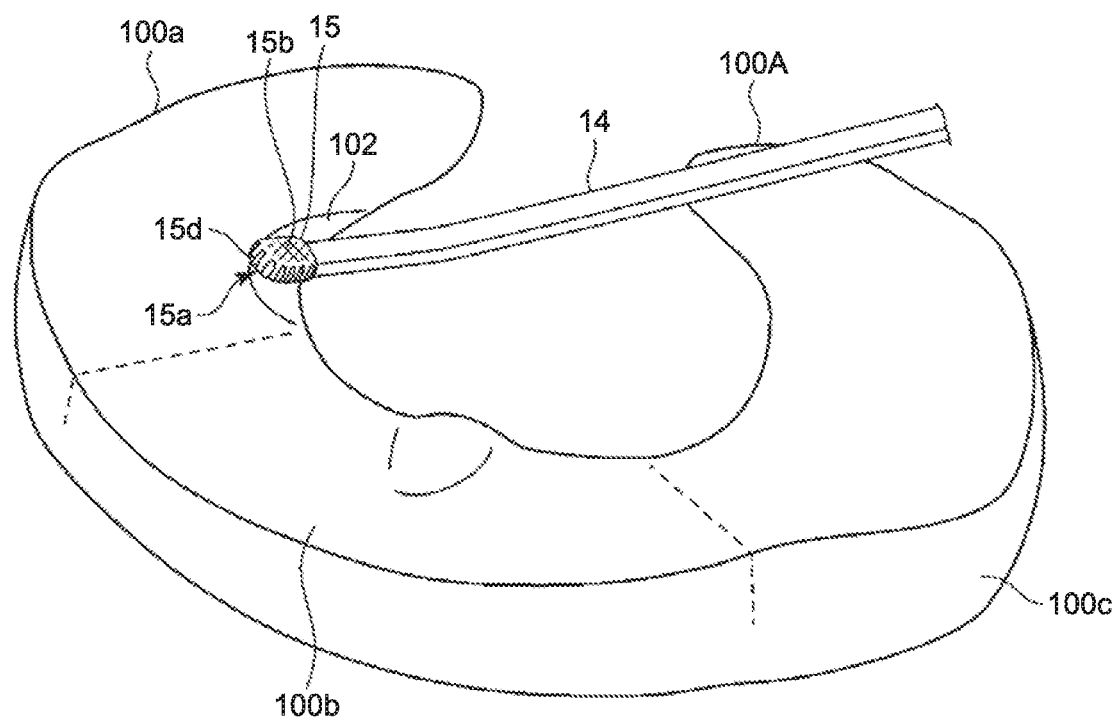
FIG. 9 is a diagram that conceptually illustrates a state of the procedure performed on the target site for procedure, which is present in the posterior portion of the lateral meniscus, using the cutting portion formed on the underside of the front end side of the procedure portion.
Figure 10:
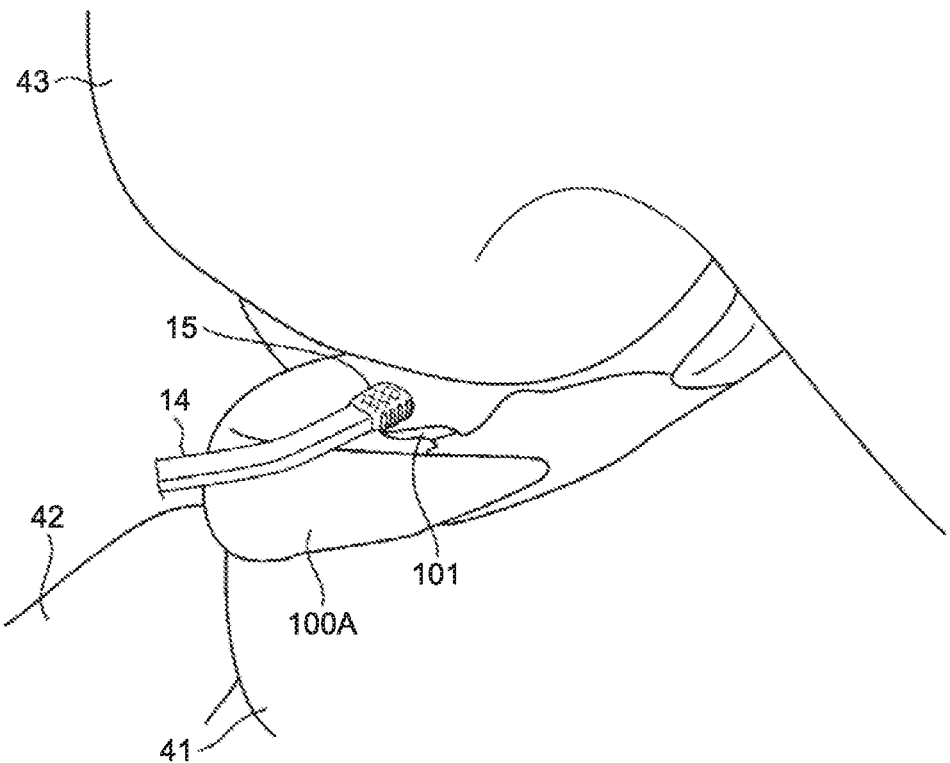
FIG. 10 is a diagram illustrating a situation in which a target site for procedure present in the body portion of the lateral meniscus between joints is subjected to a procedure using the entire surface of the cutting portion formed on the underside of the procedure portion.
Figure 11:
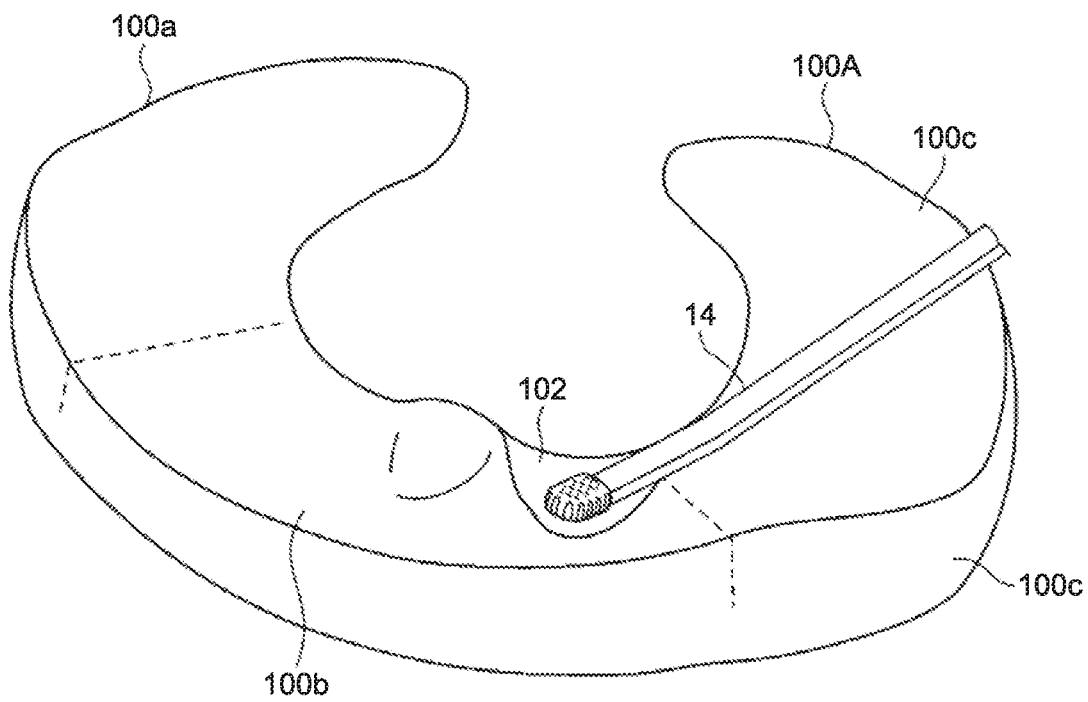
FIG. 11 is a diagram that conceptually illustrates a state of the procedure performed on the target site for procedure, which is present in the body portion of the lateral meniscus, using the entire surface of the cutting portion formed on the underside of the procedure portion.
Figure 12:
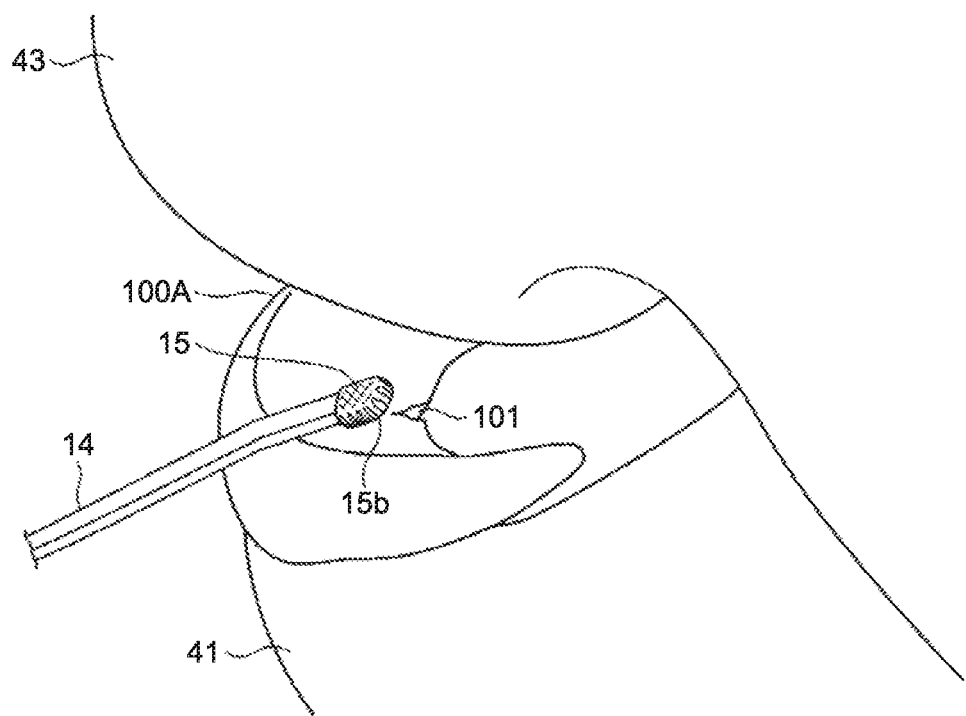
FIG. 12 is a diagram illustrating a situation in which a target site for procedure present in the anterior portion of the lateral meniscus between joints is subjected to a procedure using the entire surface of the cutting portion formed on the top surface of the procedure portion.
Figure 13:
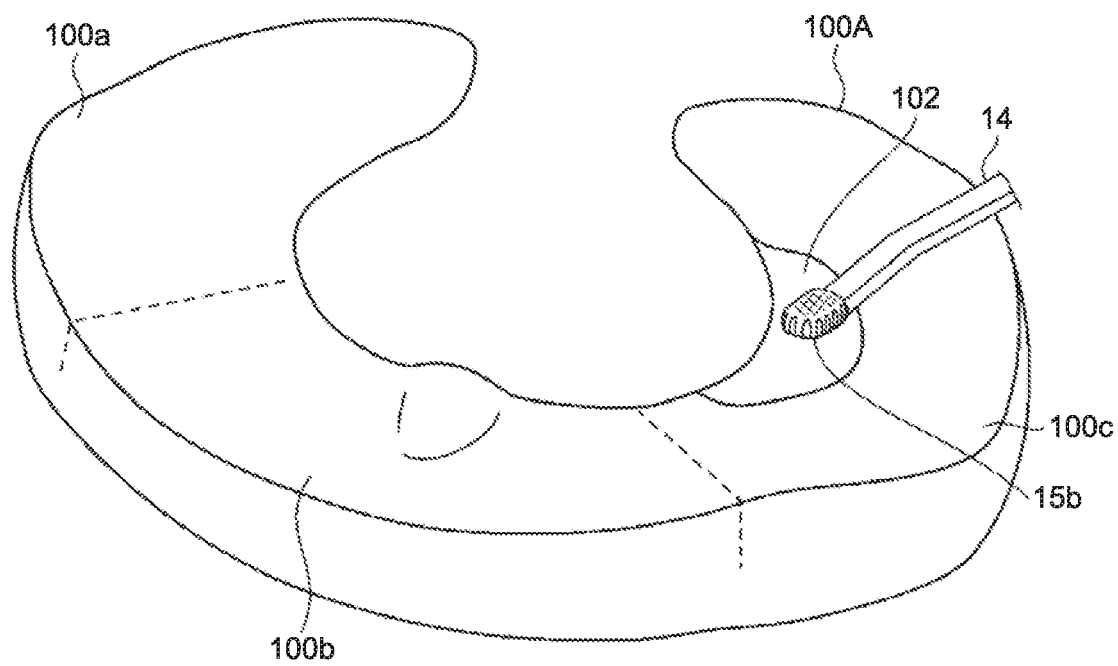
FIG. 13 is a diagram that conceptually illustrates a state of the procedure performed on the target site for procedure, which is present in the anterior portion of the lateral meniscus, using the entire surface of the cutting portion formed on the top surface of the procedure portion.

Explained below with reference to FIGS. 7 to 13 is a resection procedure performed on the damaged meniscus 100 using the surgery system 10 that includes the ultrasonic surgical tool 2 and the endoscopic system 30. FIG. 7 is a diagram that conceptually illustrates an arthroscopic surgery performed using an ultrasonic surgical tool. FIG. 8 is a diagram illustrating a situation in which a target site for procedure present in the posterior portion of the lateral meniscus between joints is subjected to a procedure using the front end side of the cutting portion formed on the underside of a procedure portion. FIG. 9 is a diagram that conceptually illustrates a state of the procedure performed on the concerned posterior portion. FIG. 10 is a diagram illustrating a situation in which a target site for procedure present in the body portion of the lateral meniscus between joints is subjected to a procedure using the entire surface of the cutting portion formed on the underside of the procedure portion. FIG. 11 is a diagram that conceptually illustrates a state of the procedure performed on the concerned body portion. FIG. 12 is a diagram illustrating a situation in which a target site for procedure present in the anterior portion of the lateral meniscus between joints is subjected to a procedure using the entire surface of the cutting portion formed on the top surface of the procedure portion. FIG. 13 is a diagram that conceptually illustrates a state of the procedure performed on the concerned anterior portion.

An exemplary embodiment is discussed below under the assumption that a horizontal rupture is developed in each portion of the meniscus 100 representing the target for procedure. In FIG. 7 is illustrated a state in which the patient has bent the knee and opened the joint region. Thus, a patellar surface 43a of the femur 43 is oriented in the anterior direction.

Firstly, the ultrasonic probe 14 is inserted from a portal 51, and the arthroscope 31 is inserted from a portal 52. The positions of the portals should be appropriately set according to the individual differences of the patient, the targets for procedure, and the procedure details.

As illustrated in FIG. 8, the ultrasonic probe 14 passes through the space in between the femur 43 and a tibia 41, and the front end thereof reaches the location of the rupture developed near the posterior portion 100a of the meniscus (lateral meniscus) 100A as illustrated in FIG. 8. In the present embodiment, the ultrasonic probe 14 has the procedure portion 15 disposed at the end that is bent upward. Hence, the procedure portion 15 can easily pass through the space in between the femur 43 and the tibia 41, and can reach the target location for procedure in the posterior portion 100a of the meniscus 100A.

With reference to FIG. 9, of the procedure portion 15 of the ultrasonic probe 14, the front end side of the apical cutting surface 15d and the lower cutting surface 15a is put in the posterior portion 100a, and the horizontal rupture 101 is resected along the inclination of the top surface of the meniscus 100A, so that the inclined resection plane 102 is formed.

Then, as illustrated in FIG. 10, the procedure portion 15 is moved to the target location for procedure represented by the horizontal rupture 101 developed near the middle portion 100b of the meniscus 100A. With reference to FIG. 11, of the procedure portion 15, the lower cutting surface 15a is applied to the target location for procedure represented by the rupture 101 of the meniscus 100B, and the horizontal rupture is resected along the inclination of the top surface of the meniscus 100A, so that the inclined resection plane 102 is formed while ensuring that no horn portions are developed.

Subsequently, as illustrated in FIG. 12, the procedure portion 15 is moved to the target location for procedure represented by the horizontal rupture 101 developed near the anterior portion 100c of the meniscus 100A. While moving the procedure portion 15, the operator inverts the ultrasonic probe 14 and holds it with the bend of the bent portion oriented downward. As a result of changing the holding pattern, the cutting surface 15b that was the top surface of the procedure portion 15 changes to be the under surface, and thus faces the target location for procedure. Because of the inversion of the bent portion, as compared to the cutting-plane angle of the cutting surface 15a, the cutting plane of the cutting surface 15b becomes a larger angle approaching the vertical direction. That is, the angle at which the procedure portion 15 makes surface contact with the target site for procedure increases in inclination from 10° to 20°, for example.

With reference to FIG. 13, of the procedure portion 15, the cutting surface 15b is applied to the target location for procedure represented by the rupture 101 of the meniscus 100B, and the horizontal rupture 101 is resected along the inclination of the top surface of the meniscus 100A, so that the inclined resection plane 102 is formed while ensuring that no horn portions are developed.

Figure 14:
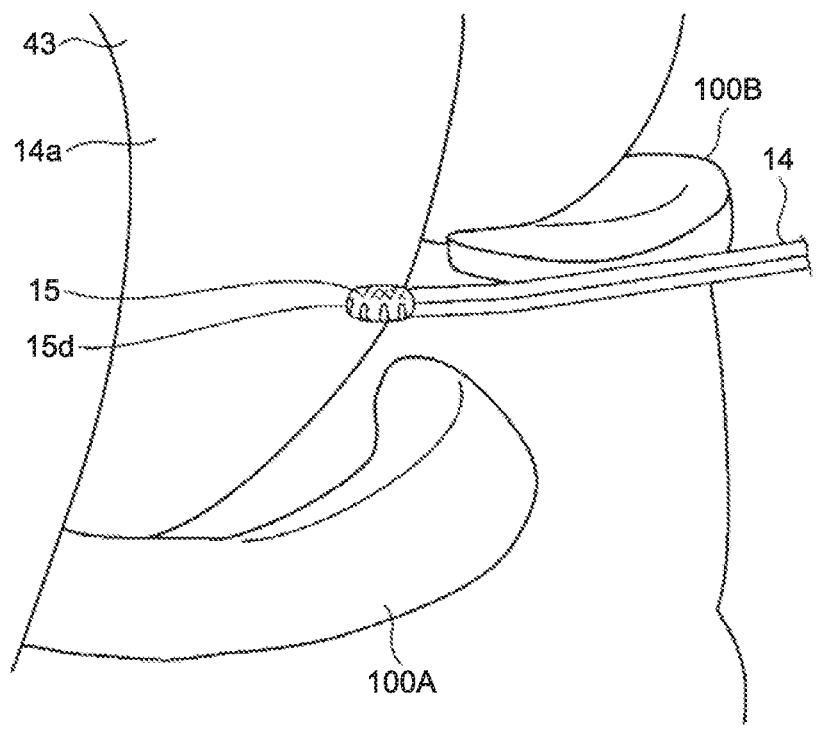
FIG. 14 is a diagram that conceptually illustrates a state of the procedure performed on a cartilage formed on the underside of the joint of the femur.

Meanwhile, the target sites for procedure are not limited to the meniscus. As illustrated in FIG. 14, using the apical cutting surface 15d of the procedure portion 15 of the ultrasonic probe 14, it also becomes possible to resect a cartilage formed on the patellar surface 43a of the femur 43.

According to the present embodiment, a cutting procedure on the target sites for procedure can be performed using the principal surfaces formed on the upper side and the lower side of the ultrasonic probe, using both lateral surfaces, and using the apical surface. Hence, even if the approach is from the same portal, by changing the posture of the ultrasonic probe, the reachable range of the procedure portion 15 becomes wider thereby widening the procedure range. As a result, the desired cutting procedure can be performed without having to open new portals.

Given below is the explanation of another exemplary embodiment.

Figure 15:
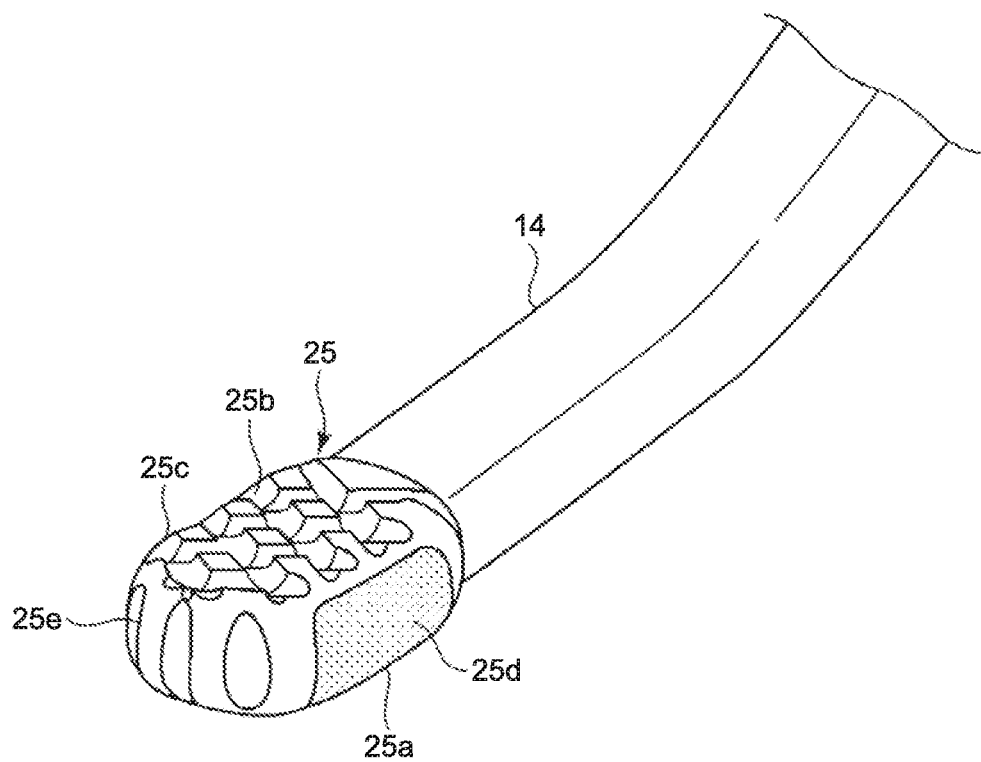
FIG. 15 is a diagram illustrating the external shape of a procedure portion of the ultrasonic probe according to an embodiment, when viewed from an obliquely upward direction.

FIG. 15 is a diagram illustrating the external shape of a procedure portion of the ultrasonic probe according to the present embodiment, when viewed from an obliquely upward direction. The ultrasonic probe of this embodiment, except for the procedure portion, is equivalent to the above embodiment. Hence, the same explanation is not given again.

In a procedure portion 25 of the ultrasonic probe 14 according to the present embodiment, a cutting surface 25a that is meant for rough cutting and that is made of a corrugated surface having a crosshatch pattern or a twill line pattern due to a plurality of U-shaped grooves is formed on the lower principal surface. In an identical manner, a cutting surface 25b that is made of a corrugated surface having a crosshatch pattern or a twill line pattern is formed on the upper principal surface.

Moreover, on one lateral surface of the procedure portion 25, for example, a raspatory surface 25d can be formed by cohesively using granular diamond or borazon abrasive grain. Furthermore, on the lateral surface is formed a lateral cutting surface 25c in which a plurality of U-shaped grooves is arranged in a flounder pattern. Moreover, on the anterior surface (the apical surface) is formed an apical cutting surface 25e in which a plurality of U-shaped grooves is arranged in a flounder pattern. Furthermore, when an operator holds the ultrasonic probe 14 in the normal holding pattern in which the cutting surface 25a (described later) is on the underside, the front end side of the ultrasonic probe 14 is bent upward in such a way that the probe main body 14 bends backward at a position away by about 10 mm from the front end of the procedure portion 25. Meanwhile, the raspatory surface 25d formed by cohesively using granular diamond or borazon abrasive grain can be adapted in other exemplary embodiments too.

According to the present embodiment, because of the procedure portion 25 of the ultrasonic probe 14, in the cutting procedure, operations from rough cutting to finishing of the target site for procedure can be performed using only a single ultrasonic probe without having to replace it. As a result, the surgery can be continued without any interruption for probe replacement, thereby enabling achieving reduction in the time and efforts of the operator and shortening of the period of time taken for surgery. Particularly, in the ultrasonic probe 14 according to the present embodiment, since the probe main body on the near side is configured to have a bent shape, when the insertion path inside a joint is curved, the procedure portion 25 can be inserted using the bend thereby enabling achieving enhancement in the accessibility.

In the exemplary embodiments described above, the ultrasonic probe 14 is configured to have a bent shape. However, the ultrasonic probe 14 need not always be bent. For example, at the time of resecting a bony spur, it is expected to use a probe not having any bends. Moreover, because of not having any bends, when there are different cutting blades for all cutting surfaces, it becomes possible to deal with various procedures.

Given below is the explanation of another exemplary embodiment.

Figure 16:
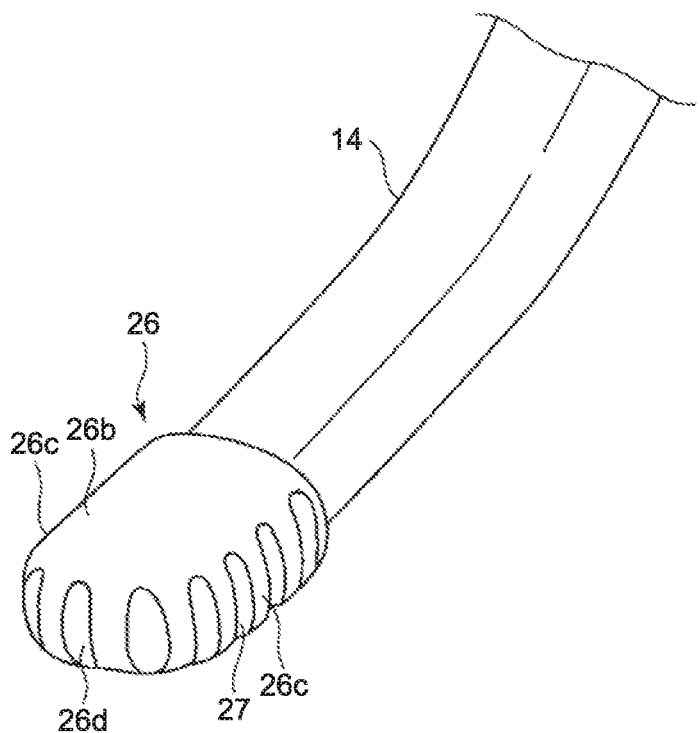
FIG. 16 is a diagram illustrating the external shape of a procedure portion of the ultrasonic probe according to an embodiment, when viewed from an obliquely upward direction.
Figure 17:
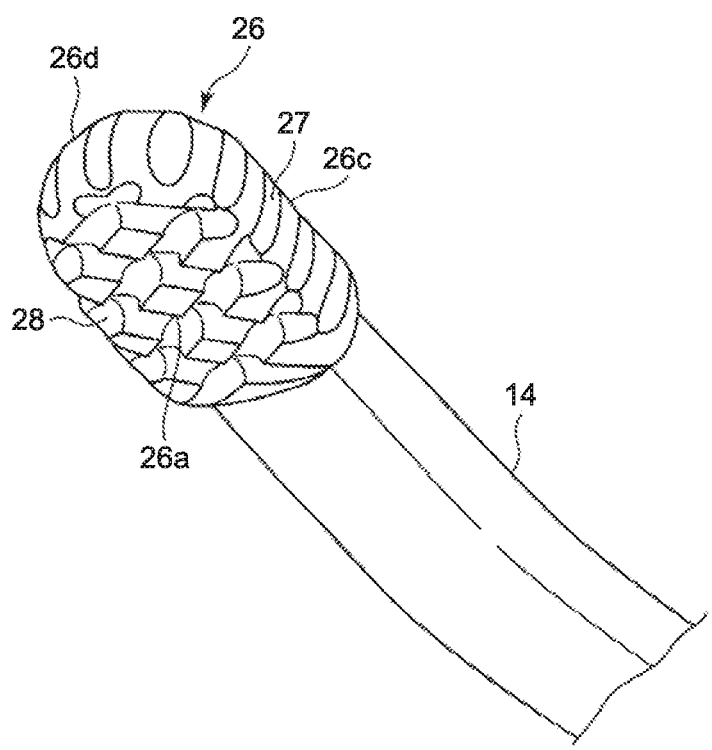
FIG. 17 is a diagram illustrating the external shape of the procedure portion illustrated in FIG. 16, when viewed from an obliquely downward direction.

FIG. 16 is a diagram illustrating the external shape of a procedure portion of the ultrasonic probe according to this embodiment, when viewed from an obliquely upward direction. FIG. 17 is a diagram illustrating the external shape of the procedure portion illustrated in FIG. 16, when viewed from an obliquely downward direction. The ultrasonic probe of the present embodiment, except for the procedure portion, is equivalent to the above embodiment. Hence, the same explanation is not given again.

As illustrated in FIGS. 16 and 17, in a procedure portion 26, a cutting surface 26a that is made of a corrugated surface having a crosshatch pattern due to a plurality of U-shaped grooves 28 is formed on the lower principal surface (the under surface). However, there is no cutting surface formed on the upper principal surface. Thus, the procedure portion 26 is equivalent to the configuration in which the procedure portion 15 illustrated in FIG. 3 does not have a cutting surface formed on the top surface.

Moreover, in the procedure portion 26, a plurality of vertical U-shaped grooves 27 are formed in a flounder pattern on both lateral surfaces and the anterior surface (the apical surface), thereby resulting in the formation of cutting surfaces 26c and 26e. The arrangement of the U-shaped grooves 27 and the U-shaped grooves 28 is such that a flounder pattern, a crosshatch pattern, or a twill line pattern is formed. Moreover, the U-shaped grooves 27 as well as the U-shaped grooves 28 either can be arranged at regular intervals or can be arranged with different intervals set therebetween.

When an operator holds the ultrasonic probe 14 in the normal holding pattern in which the cutting surface 26a (described later) is on the underside, the front end side of the ultrasonic probe 14 is bent upward in such a way that the probe main body 14 bends backward at a position away by about 10 mm from the front end of the procedure portion 26.

According to the present embodiment, apart from the fact that resection is performed using only one principal surface, it becomes possible to achieve the identical actions and effect to the embodiment described above.

Given below is the explanation of another exemplary embodiment.

Figure 18:
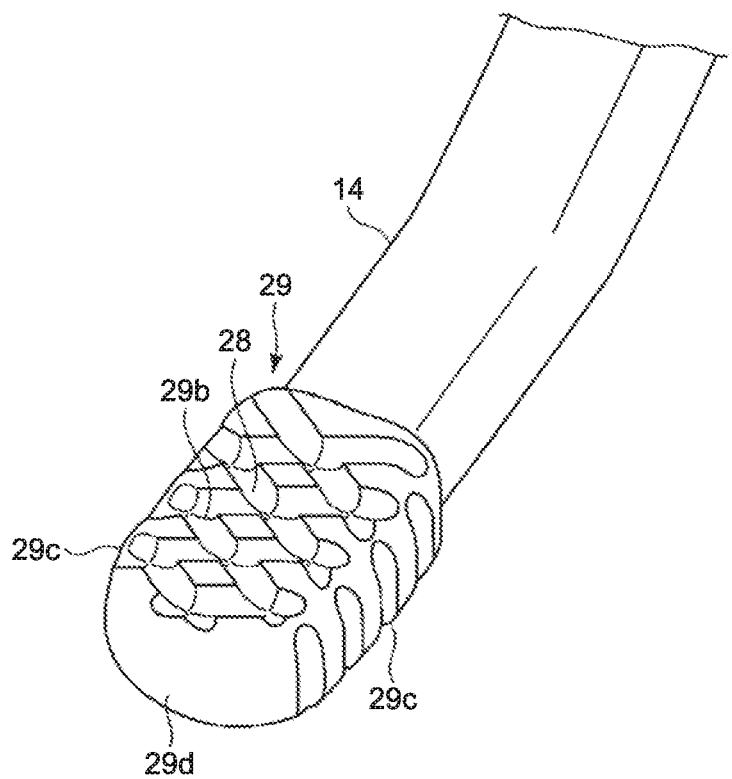
FIG. 18 is a diagram illustrating the external shape of a procedure portion of the ultrasonic probe according to an embodiment, when viewed from an obliquely upward direction.
Figure 19:
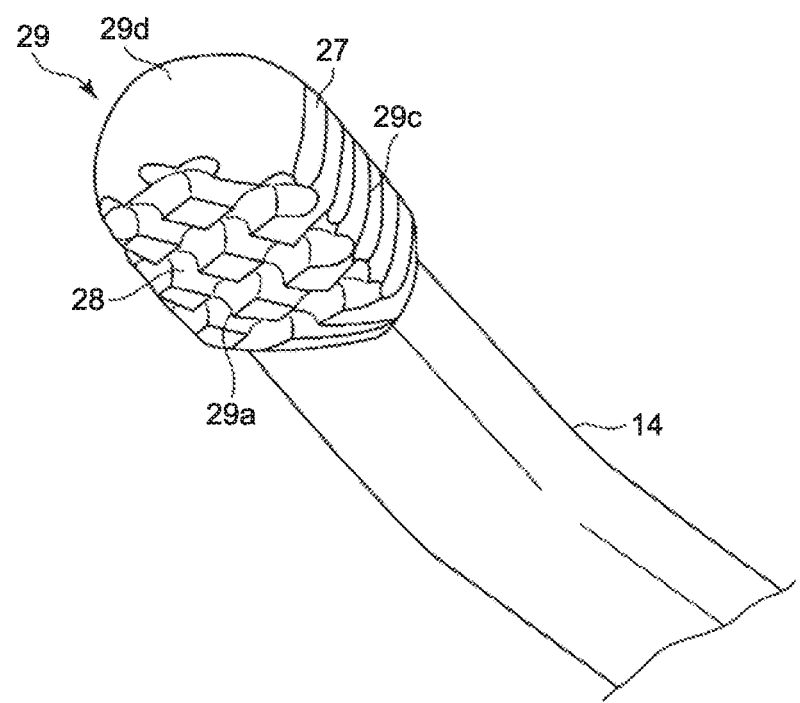
FIG. 19 is a diagram illustrating the external shape of the procedure portion illustrated in FIG. 18, when viewed from an obliquely downward direction.

FIG. 18 is a diagram illustrating the external shape of a procedure portion of the ultrasonic probe according to the present embodiment, when viewed from an obliquely upward direction. FIG. 19 is a diagram illustrating the external shape of the procedure portion illustrated in FIG. 18, when viewed from an obliquely downward direction. The ultrasonic probe of the present embodiment, except for the procedure portion, is equivalent to the above embodiment. Hence, the same explanation is not given again.

In a procedure portion 29 of the ultrasonic probe 14, cutting surfaces 29a and 29b that are made of corrugated surfaces having a crosshatch pattern due to the plurality of U-shaped grooves 28 are formed on the lower principal surface and the upper principal surface, respectively. The arrangement of the U-shaped grooves 28 is such that a flounder pattern, a crosshatch pattern, or a twill line pattern is formed. Moreover, the U-shaped grooves 28 either can be arranged at regular intervals or can be arranged with different intervals set therebetween.

Moreover, on both lateral faces of the procedure portion 29, lateral cutting surfaces 29c are formed in which the plurality of U-shaped grooves 27 is arranged in a seriate flounder pattern in the vertical direction (the thickness direction). However, there is no cutting surface formed on the anterior surface (the apical surface).

When an operator holds the ultrasonic probe 14 in the normal holding pattern in which the cutting surface 29a (described later) is on the underside, the front end side of the ultrasonic probe 14 is bent upward in such a way that the probe main body 14 bends backward at a position away by about 10 mm from the front end of the procedure portion 29.

According to the present embodiment, apart from eliminating the cutting using the front end, it becomes possible to achieve the identical actions and effect to the embodiment described above. Moreover, this ultrasonic probe 14 is suitable for such target sites for procedure in which even though the front end of the procedure portion makes contact, the location of contact is not to be cut.

Meanwhile, in the above exemplary embodiments, the explanation is given for an example in which the procedure portion is cuboid in shape with rounded corners (having only rectangular surfaces, or a box shape enclosed by rectangular surfaces or square surfaces). However, that is not the only possible case. Herein, the surface at which the procedure portion and the target site for procedure come in contact is treated as the bottom surface.

Thus, the procedure portion having a cuboid shape is formed using the surfaces formed by the sides present in the direction orthogonal to the longitudinal axis of the probe main body. Alternatively, using the surfaces such as trapezoids formed by the sides present in the directions intersecting with the longitudinal axis of the probe main body, the procedure portion having the shape of a quadratic prism can be formed. For example, the surface on which the procedure portion is to be formed can be of a box shape formed by combining trapezoids. For example, when the two principal surfaces (15a and 15b) have a trapezoidal shape, a quadratic prism is obtained whose front end side in the width direction has a narrowing shape or an expanding shape in the width direction. When both lateral surfaces have a trapezoidal shape, a quadratic prism is obtained that becomes smaller or bigger in the thickness direction of the front end side. Of course, it is possible to have a quadratic prism in which the two principal surfaces and both lateral surfaces have a trapezoidal surface shape.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for performing a procedure on a meniscus, using an ultrasonic surgical tool,
the method comprising:
inserting a probe of the ultrasonic surgical tool in a body, the probe having an elongated shaft shape and being configured to transmit ultrasonic vibration from a proximal end to a front end, the probe comprising a bent portion that is inclined with respect to a longitudinal axis of a probe main body, and a procedure portion disposed at the front end of the probe and comprising a plurality of cutting surfaces;
moving the probe through a space in between a femur and a tibia to position the procedure portion adjacent to a horizontal rupture in the meniscus;
positioning a cutting surface of the procedure portion on a posterior portion of the meniscus; and
resecting the horizontal rupture via the cutting surface along an inclination of the meniscus to form an inclined resection plane.

2. The method according to claim 1, further comprising:
moving the probe such that the procedure portion is positioned adjacent to a second horizontal rupture near a middle portion of the meniscus;
positioning a cutting surface of the procedure portion on the second horizontal rupture in the meniscus; and
resecting the horizontal rupture along an inclination of the meniscus using the cutting surface of the procedure portion to form a second inclined resection plane while ensuring that no horn portion is developed in the meniscus.

3. The method according to claim 1, further comprising:
moving the probe to position the procedure portion adjacent to another horizontal rupture developed near an anterior portion of the meniscus.

4. The method according to claim 1,
wherein the inclined resection plane is formed while ensuring that no horn portion is developed in the meniscus.

5. The method according to claim 1, further comprising inverting the probe to change an orientation of the bent portion of the probe before resecting the horizontal rupture.

6. The method according to claim 5, wherein an angle at which the procedure portion makes surface contact with the horizontal rupture increases in inclination due to inverting the probe.

7. The method according to claim 1, wherein the procedure portion comprises a lower cutting surface and lateral cutting surfaces.

8. The method according to claim 1, wherein the plurality of cutting surfaces comprises at least two of a lower cutting surface, an upper cutting surface, an apical cutting surface, and a lateral cutting surface.

9. The method according to claim 8, wherein the plurality of cutting surfaces of the procedure portion does not include the apical cutting surface.

10. The method according to claim 1, wherein the cutting surfaces are corrugated surfaces.

* * * * *